United States Patent [19]

Campos

[11] 4,194,628
[45] Mar. 25, 1980

[54] MEDICAL CASE

[76] Inventor: Juan M. Campos, 804 S. Main St., McAllen, Tex. 78501

[21] Appl. No.: 943,321

[22] Filed: Sep. 18, 1978

[51] Int. Cl.² ................... A45C 11/00; A61B 19/00
[52] U.S. Cl. ..................................... 206/570; 190/9
[58] Field of Search .............. 206/570, 370, 372, 373, 206/526, 572; 190/1, 9, 42

[56] References Cited

U.S. PATENT DOCUMENTS

| | | | |
|---|---|---|---|
| 369,438 | 9/1887 | De Myers | 206/572 |
| 505,222 | 9/1893 | Hoff | 206/570 |
| 1,184,494 | 5/1916 | Sorensen | 206/572 |
| 1,374,849 | 4/1921 | Greene | 206/570 |
| 1,727,235 | 9/1929 | Joyse | 206/572 |
| 1,876,493 | 9/1932 | Frutkow | 206/572 |
| 2,094,805 | 10/1937 | Meier | 206/373 |
| 3,082,567 | 3/1963 | Gee | 190/1 |

*Primary Examiner*—Herbert F. Ross
*Attorney, Agent, or Firm*—Cox & Smith, Incorporated

[57] ABSTRACT

A medical case for storage of medical supplies and for administering medical treatment having a central storage section with an enlarged base portion and two side sections hinged to the enlarged base portion so that the side sections form a continuous base support surface with the enlarged base portion.

1 Claim, 5 Drawing Figures

MEDICAL CASE

BACKGROUND OF THE INVENTION

This invention relates generally to medical cases and in particular medical cases for storage of medical supplies and also for use in administering medical treatment to a patient.

It has been known in the prior art to provide cases for the storage of medical supplies and also for treating patients. Such cases have been portable so that they may be transported to a remote location for treating a patient at the site of injury or illness. Examples of known U.S. Patents relating to medical cases and the like are as follows: U.S. Pat. Nos. 42,943; 1,727,235; 2,055,657; 2,135,238; 2,183,663; 2,357,555; 2,370,941; 2,801,738; 2,870,904; and 2,998,583.

It is an object of the invention to provide a medical case which is easily transportable and which also may be used for facilitating and administering treatment to a patient. It is also an object to provide a medical case which, when used to administer treatment to a patient, is stable to avoid tipping over of the case. Another object is to provide a case which utilizes maximum storage capacity of the case while at the same time providing ready accessibility to each and every item in the case. As shown by the above listed patents, numerous attempts have been made over long periods of time to provide a medical case which solves the problems of storing medical gear and treating a patient at the location of injury or illness. It is accordingly an object of the present invention to overcome the problems which have not yet been solved by the prior art and to provide a case which will fulfill a long-felt need for use at a remote location in the field to administer treatment to a sick or injured patient.

SUMMARY OF THE INVENTION

A new and improved medical case having a central storage section for storing supplies in each side thereof and an enlarged base portion to provide a sturdy support for the central section and to stabilize the central section. Side sections having storage compartments therein are connected by hinges to the enlarged base portion so that the side sections form a continuation of the enlarged base portion to further stabilize the case when the side sections are in the open position. Transparent covers are provided for each storage section which at the same time allow ready viewing of the articles. When the side sections are pivoted to their closed positions with the central section, a substantially rectangular case is formed. An extended rod is provided for supporting bottles or the like from the case for administering treatment to a patient.

BRIEF DESCRIPTION OF THE PREFERRED EMBODIMENT

Figure 1:
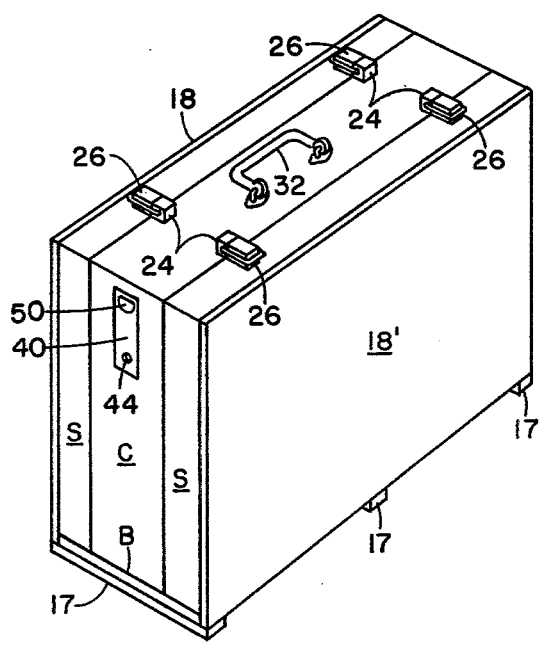
FIG. 1 shows the medical case of the invention.
Figure 3:
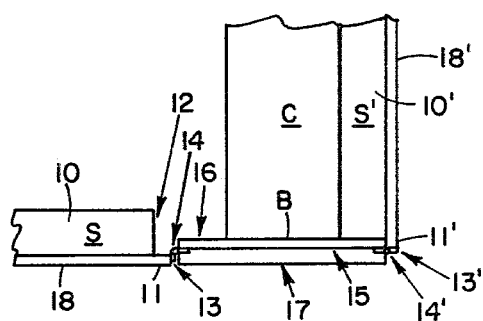
FIG. 3 is a partial side view showing the enlarged base portion of the central section and the construction of the side sections and hinges.

Referring to FIG. 1 of the drawings, there is shown the medical case of the invention. The medical case includes a central section C and an enlarged base portion B for supporting the case. The connection of the side sections to the enlarged base portion is shown in greater detail in FIGS. 2 and 3.

Figure 2:
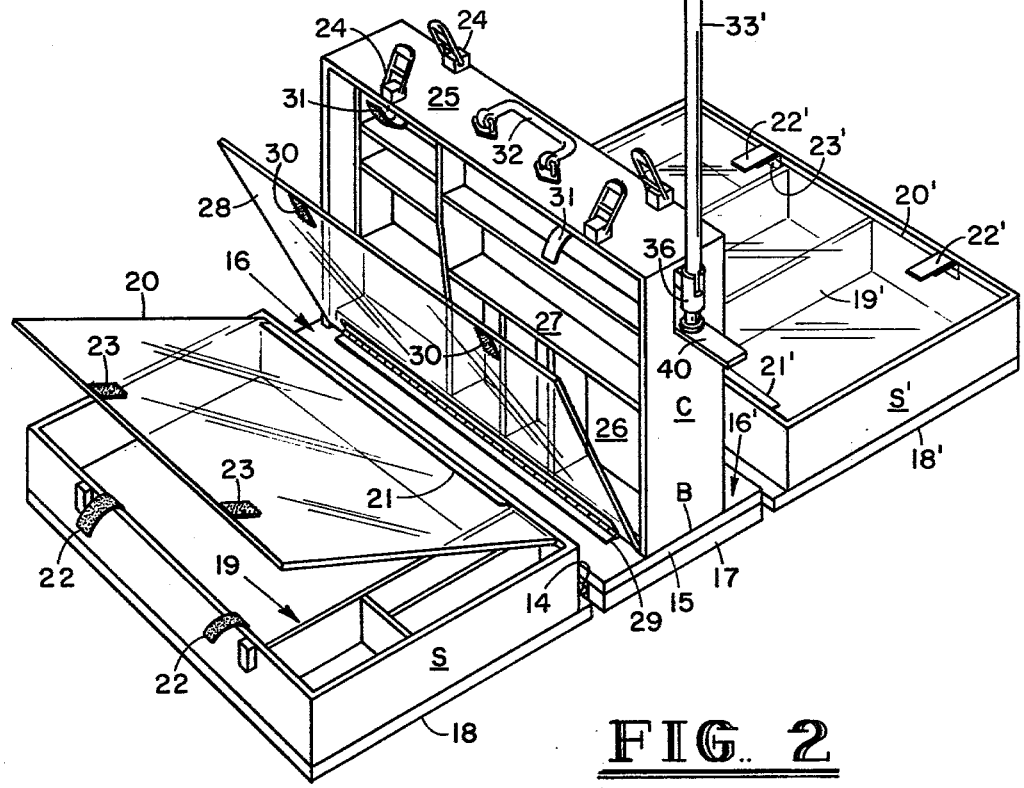
FIG. 2 shows the side sections moved to their open position for administering treatment to a patient and with the rod extended for holding bottles.

The side sections S and S' are substantially identical in construction so only one of the side sections is described in detail with similar components of the other side section being designated by the same reference numeral with the superscript "'" used in connection with the common reference numerals. The side section S includes a main portion 10 which includes an extension 11 extending downwardly therefrom. The lower portion 12 of the main portion 10 is recessed from the end 13 of the extension 11. A piano-type hinge 14 is secured to the surface 13 of the extension 11 and to the lower surface 15 of the enlarged base portion B. The base portion B includes an extended portion 16 to which is attached the hinge 14. Secured to the lower surface 15 are a plurality of narrow strips or supports 17, one of which is shown. The thickness of the extension 11 is about the same as the thickness of the narrow strips 17 so that the outer wall 18 of the side section forms a continuous base support surface with the narrow strips 17 when the side section is moved to its open position as shown in FIG. 2. The side section S' includes components similar to those described above with reference numerals 10 through 18, and the similar components are designated with similar numerals 10' through 18'.

As shown in FIG. 2, when both the side section S and S' are moved to their open positions, a continuous support surface is provided in the medical case. This provides extra stability to the case so that it is unlikely that the case will be tipped over when administering treatment to a patient. When the side sections are in their closed positions, they interfit with the extension 16 of the enlarged base portion of the central section so as to provide a substantially rectangular case.

The side section S includes a plurality of dividers 19 which serve to separate different medical devices or medicines which are placed in the section. A transparent cover 20 is connected to the side section S through hinge means 21 to provide it a cover for the side section S. Suitable complementary fastening means 22 and 23, such as Velcro fasteners, maintain the transparent cover in its closed position as best shown with the side section S' in FIG. 2. The transparent cover 20 allows ready viewing of the devices or medicines which are placed in the divided sections of the side section while still preventing them from falling from the side section when the side section is moved to its closed position shown in FIG. 1 or when the case is tipped over. Latches 24 are secured to the upper surface 25 of the central section. Complementary catches 26 are connected with the side sections S and S' for securing with the latches 24 to maintain the side sections S and S' in their closed positions as best shown in FIG. 1.

The central section C is separated into two halves by wall member 26. Suitably oriented dividers 27 are provided on each side of the wall member 26 for the storage of medicine or medical devices. The orientation of the dividers 27 is such that the desired medical devices or medicine may be positioned in the compartments formed by the dividers so as to maintain each medical device or medicine separate. A transparent cover 28 is secured by hinged means 29 to the central section, as are the transparent covers 20 and 20'. It is understood that a second transparent cover (not shown) is also secured to the other side of the central section for maintaining articles in the dividers (not shown) on the side (not shown) of the wall member 26. Complementary fasteners 30 and 31, such as Velcro fasteners, maintain the cover 28 in a closed position to prevent medical devices or medicine from falling from the compartments formed by the dividers 27. A suitable handle means 32 is provided for carrying the medical case.

Figure 4:
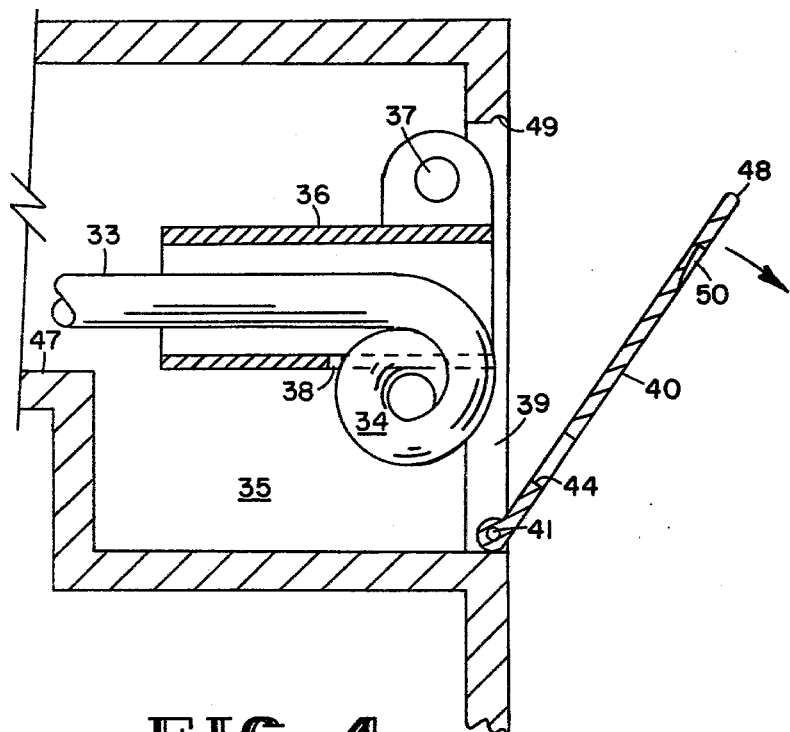
FIG. 4 is a partial cross-section showing the support rod and its storage position.
Figure 5:
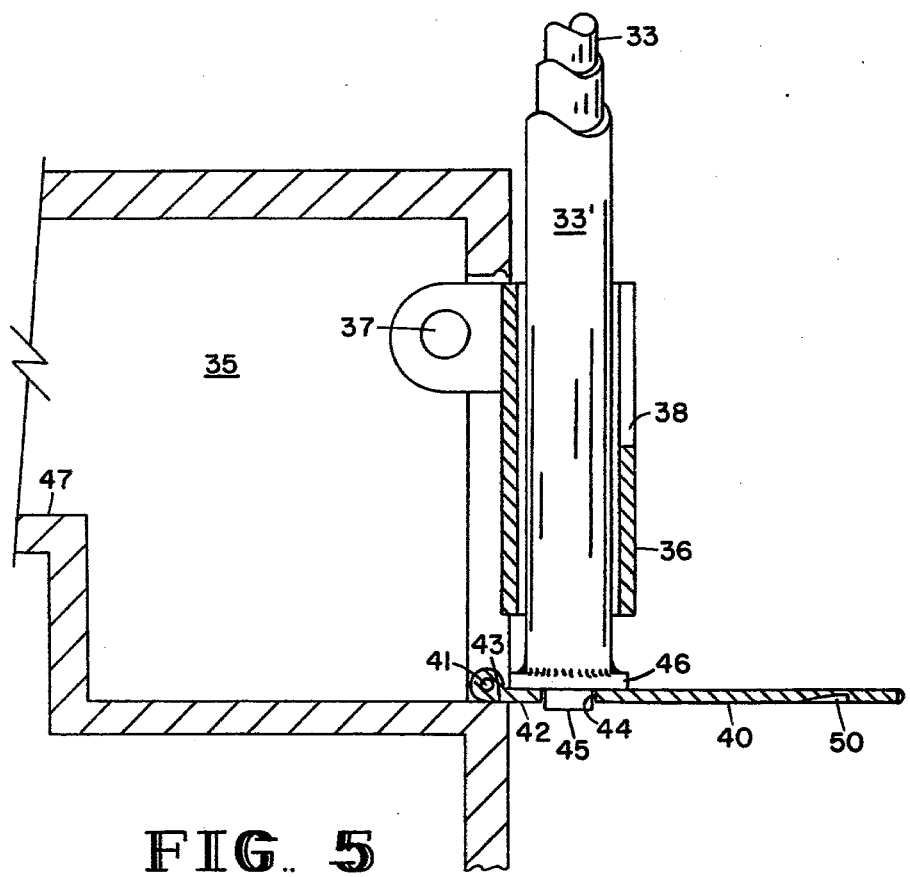
FIG. 5 is a partial cross-sectional view showing the support rod in its extended position for administering treatment to a patient.

A telescoping rod 33 is provided for hanging of bottles or the like for administering treatment to a patient. The telescoping rod 33 comprises a plurality of sections with a coiled portion 34 at the outer end. As best shown in FIGS. 4 and 5, an enlarged portion 35 is provided for receiving the pivoted mount bracket 36, which is pivotally mounted about pivot pin 37 to the medical case. Mount bracket 36 is tubular in construction and includes a notched-out portion 38 for receiving the coiled end 34, as shown in FIG. 4. An opening 39 is provided in the medical case, which opening is closed by a door member 40, which is pivoted about pin 41. The pivot pin 41 is positioned so that the door 40 will only pivot to the position shown in FIG. 5, since the lower edge 42 of the door 40 rests against the edge 43 of the enlarged opening 35. The door 40 includes an aperture 44 for receiving a pin 45 secured with the base support 46 of the telescoping rod 33.

The telescoping rod 33 extends through the central portion substantially the entire length thereof in its storage position. A channel 47 is provided for receiving the telescoping rod. The end 48 of the door member 40 includes a rounded portion, which is received in recessed portion 49 in the opening 39 to retain the door in its storage position, as shown in FIG. 1. Another recess 50 in the door 40 allows pulling of the door 40 to its open position shown in FIG. 5.

When it is desired to utilize the telescoping rod 33, the door 40 is pulled open to the position shown in FIG. 5, so that the telescoping rod may be pulled outwardly with the coiled end 34, until the base portion 33' is positioned within the mount bracket 36. The rod 33 may then be telescoped to its extended position as shown in FIG. 2, and the base portion 33' may be dropped to where the pin 45 inserts in the aperture 44 to retain the telescoping rod in position. This prevents the bracket 36 from pivoting about pin 37. When it is desired to reposition the telescoping rod 33 to its stored position, it may be lifted upwardly, until the pin 35 clears the aperture 44, so that the bracket 36 may be pivoted to its position shown in FIG. 4 and the telescoping rod may be slid inwardly in the channel 47. The door 40 may then be closed, as shown in FIG. 1. The case is ready for storage or transport.

While there has been shown and described a preferred embodiment of a medical case in accordance with the invention, it will be appreciated that many changes and modifications may be made therein without, however, departing from the essential spirit of the invention within the scope of the claims.

I claim:

1. A medical case for storage of medical supplies and for administering medical treatment to a patient, comprising:

a central section having a vertically extending storage portion;

said central section having a base support portion extending past each side of the central section to provide an enlarged support to stabilize the central section;

side sections having storage portions secured to each side of the base support portion by hinge means to provide a substantially rectangular case in their upright closed position and with the outer portions of the side sections forming a continuous support portion with the base support portion in the open, substantially horizontal, positions;

the side sections including extensions hingedly connected to the base support portion;

the central section and side sections having transparent covers over the storage portions to retain articles therein;

the storage portions of the side sections are positioned above the base support portion in the closed position;

a suport rod extending generally vertically above the case during use for administering medicine to a patient by hanging medical means on the support rod;

the support rod having telescoping sections and pivotally mounted horizontally inside said central section for storing the support rod in the case; and the medical case having a channel open at one side of said central section for receiving the support rod for storage inside the case and a pivotal door closing said channel opening and providing a base for said rod when in use.

* * * * *